(12) United States Patent
Boenitz-Dulat et al.

(10) Patent No.: US 10,190,182 B2
(45) Date of Patent: Jan. 29, 2019

(54) METHODS FOR ENZYME MEDIATED POLYPEPTIDE CONJUGATION

(71) Applicant: Hoffmann-La Roche Inc., Little Falls, NJ (US)

(72) Inventors: Mara Boenitz-Dulat, Tutzing (DE); Peter Kratzsch, Penzberg (DE); Martin Schatte, Karlsbad (DE)

(73) Assignee: HOFFMANN LA-ROCHE INC., Little Falls, NJ (US)

( * ) Notice: Subject to any disclaimer, the term of this patent is extended or adjusted under 35 U.S.C. 154(b) by 42 days.

(21) Appl. No.: 15/625,975

(22) Filed: Jun. 16, 2017

(65) Prior Publication Data

US 2017/0292166 A1 Oct. 12, 2017

Related U.S. Application Data

(63) Continuation of application No. PCT/EP2015/079617, filed on Dec. 14, 2015.

(30) Foreign Application Priority Data

Dec. 17, 2014 (EP) .................................. 14198532

(51) Int. Cl.
| | |
|---|---|
| *C12N 9/52* | (2006.01) |
| *C07K 16/00* | (2006.01) |
| *C12N 9/64* | (2006.01) |
| *C07K 16/32* | (2006.01) |
| *C07K 16/46* | (2006.01) |

(52) U.S. Cl.
CPC ........ *C12Y 304/2207* (2013.01); *C07K 16/00* (2013.01); *C07K 16/32* (2013.01); *C07K 16/46* (2013.01); *C12N 9/52* (2013.01); *C12N 9/6472* (2013.01); *C07K 2317/52* (2013.01)

(58) Field of Classification Search
CPC ............................ C12N 9/52; C12Y 304/2207
See application file for complete search history.

(56) References Cited

FOREIGN PATENT DOCUMENTS

| WO | 2010/099536 A2 | 2/2010 |
|---|---|---|
| WO | 2010/099536 A3 | 2/2010 |
| WO | 2010/087994 A2 | 5/2010 |
| WO | 2013/003555 A1 | 3/2013 |
| WO | 2014/001324 A1 | 3/2014 |

OTHER PUBLICATIONS

Huang et al. 2003; Kinetic mechanism of *Staphylococcus aureus* Sortase SrtA. Biochemistry. 42: 11307-13115.*

Clancy et al., "Sortase transpeptidases: Insights into mechanism, substrate specificity, and inhibition" Biopolymers 94(4):385-396 ( 2010).
Li et al., "Irreversible Site-Specific Hydrazinolysis of Proteins by Use of Sortase" Angewandte Chemie International Edition in English 53:2198-2202 ( 2014).
Marvin et al., "Recombinant approacehs to IgG-like bispecific antibodies" Acta Pharmacologica Sinica 26(6):649-658 (Jun. 2005).
Meissner, P. et al. et al., "Transient gene expression: recombinant protein production with suspension-adapted HEK293-EBNA cells" Biotechnol Bioeng 75:197-203 ( 2001).
Ta et al., "Enzymatic Single-Chain Antibody Tagging" Circulation Research 109:365-373 (2011).
Biswas et al., "Sorting of LPXTG Peptides by Archetypal Sortase A: Role of Invariant Substrate Residues in Modulating the Enzyme Dynamics and Conformational Signature of a Productive Substrate" Biochemistry 53(15):2515-2524 ( 2014).
International Search Report of PCT/EP2015/079617 dated Mar. 17, 2016.
Levary et al., "Protein-Protein Fusion Catalyzed by Sortase A" PLoS One 6(4 Suppl e18342):1-6 (Apr. 2011).
Madej et al., "Engineering of an Anti-Epidermal Growth Factor Receptor Antibody to Single Chain Format and Labeling by Sortase A-Mediated Protein Ligation" Biotechnology and Bioengineering 109(6):1461-1470 (Jun. 2012).
Marraffini et al., "Anchoring of Surface Proteins to the Cell Wall of *Staphylococcus aureus*" Journal of Biological Chemistry 279(36):37763-37770 (Sep. 3, 2004).
Popp et al., "Making and Breaking Peptide Bonds: Protein Engineering Using Sortase" Angew. Chem. Int. Ed. 50:5024-5032 (2011).
Strijbis et al., "Protein Ligation in Living Cells Using Sortase" Traffic 13:780-789 (2012).
Ton-That et al., "Purification and Characterization of Sortase, the Transpeptidase that Cleaves Surface Proteins of *Staphylococcus aureus* at the LPXTG Motif" PNAS 96(22):12424-12429 (Oct. 26, 1999).
Tsukiji et al., "Sortase-Mediated Ligation: A Gift from Gram-Positive Bacteria to Protein Engineering" ChemBioChem 10:787-798 (2009).
Yamamura et al., "Enhancement of Sortase A-Mediated Protein Ligation by Inducing a beta-Hairpin Structure around the Ligation Site" Chem. Commun. 47:4742-4744 (2011).

* cited by examiner

*Primary Examiner* — Karen Cochrane Carlson
(74) *Attorney, Agent, or Firm* — Frank JN Berendt

(57) ABSTRACT

Herein is reported a method for producing an enzymatic conjugation product of two polypeptides comprising incubating of a first polypeptide comprising the amino acid sequence LPXTG (SEQ ID NO: 20, wherein X can be any amino acid residue), a second polypeptide has an oligoalanine $A_m$ (m=2 (SEQ ID NO: 26), or 3 (SEQ ID NO: 27), or 4 (SEQ ID NO: 28), or 5 (SEQ ID NO: 29)) amino acid sequence at its N-terminus, a third polypeptide with sortase activity which is derived from *Staphylococcus aureus* Sortase A, and recovering the conjugate from the reaction mixture and thereby producing the enzymatic conjugation product of two polypeptides.

15 Claims, 4 Drawing Sheets

Specification includes a Sequence Listing.

METHODS FOR ENZYME MEDIATED POLYPEPTIDE CONJUGATION

CROSS REFERENCE TO RELATED APPLICATIONS

This application is a continuation of International Patent Application No. PCT/EP015/079617 filed Dec. 14, 2015, which claims priority benefit to European Patent Application No. 14198532.5 filed Dec. 17, 2014, each of which are hereby incorporated by reference in their entireties.

SEQUENCE LISTING

The instant application contains a Sequence Listing submitted via EFS-Web and is hereby incorporated by reference in its entirety. Said ASCII copy, created Jun. 12, 2017, is named P32480_US_Sequence_Listing.txt, and is 13,487 bytes in size.

FIELD OF THE INVENTION

Herein is reported an improved method for the enzymatic conjugation of two compounds via a peptide bond.

BACKGROUND OF THE INVENTION

Sortase A (SrtA) is a membrane bound enzyme which attaches proteins covalently to the bacterial cell wall. The specific recognition motif on the SrtA substrate is LPXTG, whereby the enzyme cleaves between the amino acid residues threonine and glycine. The recognition motif on the peptidoglycan is a pentaglycine motif. It has been shown that a triglycine and even a diglycine motif on the N-terminus is sufficient to support the SrtA reaction (Clancy, K. W., et al., Peptide science 94 (2010) 385-396). The reaction proceeds through a thioester acyl-enzyme intermediate, which is resolved by the attack of an amine nucleophile from the oligoglycine, covalently linking peptidoglycan to a protein substrate and regenerating SrtA. SrtA can be used to covalently conjugate chemically synthetized peptides to recombinantly expressed proteins.

In WO 2010087994 methods for ligation and uses thereof are reported. Recombinant approaches to IgG-like bispecific antibodies are reported by Marvin, J. S., et al. (Acta Pharmacol. Sinica 26 (2005) 649-658). Levary, D. A., et al. (PLoS one, 6 (2011) e18342.1-e18342.6) report protein-protein fusion catalyzed by sortase A. In WO 2013/003555 the use of sortases to install click chemistry handles for protein ligation is reported.

Strijbis, K. et al (Traffic 13 (2012) 780-789) report protein ligation in living cells using Sortase. It has been stated by them that the $Ca^{2+}$-dependent *S. aureus* sortase A is not functional intracellularly, but that the $Ca^{2+}$-independent *S. pyogenes* Sortase A is functional in the cytosol and endoplasmic reticulum (ER) lumen of both *Saccharomyces cerevisiae* and mammalian HEK293T cells.

Levary, D. A., et al., report protein-protein fusion catalyzed by Sortase A (PLOS ONE 6 (2011)). Engineering of an anti-epidermal growth factor receptor antibody to single chain format and labeling by Sortase A-mediated protein ligation is reported by Madej, M. P., et al. (Biotechnol. Bioeng. 109 (2012) 1461-1470). Ta, H. T., et al., report enzymatic single-chain antibody tagging as a universal approach to targeted molecular imaging and cell homing in cardiovascular diseases (Cir. Res. 109 (2011) 365-373). Popp, M., et al., report making and breaking peptide bonds—protein engineering using sortase (Angew. Chem. Int. Ed. Eng. 50 (2011) 5024-5032). In WO 2010/087994 methods for ligation and uses thereof are reported. Engineered proteins with high affinity for DOTA chelates are reported in WO 2010/099536.

A truncated SrtA, that lacks the N-terminal membrane-anchoring motif, has been used for cell-surface protein labeling, covalent protein immobilization and incorporation of novel functionality into proteins. However, yields of SrtA-mediated ligation are always lower than 70%, if using equimolar amounts of substrate, because the reaction is reversible. Another drawback is the hydrolysis of the reaction intermediate which leads to a LPXT product which is not the intended one. This is especially problematic by long periods of incubation with SrtA. That although means that even small amounts of SrtA left in the final product can destroy it over time; this is a big issue for biologics where quality standards are very high.

Different efforts to block the revers reactions of Sortase have been reported. Yamamura, Y., et al. (Chem. Commun. 47 (2011) 4742-4744) reported enhancement of sortase A-mediated protein ligation by inducing a beta-hairpin structure around the ligation site by introducing a β-hairpin around the recognition site of the substrate.

Sorting of LPXTG peptides by archetypal sortase A, role of invariant substrate residues in modulating the enzyme dynamics and conformational signature of a productive substrate was reported by Biswas, T., et al. (Biochem. 53 (2014) 2515-2524).

Li, Y. M., et al. report irreversible site-specific hydrazinolysis of proteins by use of Sortase (Angew. Chem. Int. Ed. Engl. 53 (2014) 2198-2202).

In WO 2014/001324 a method for selection and production of tailor-made highly selective and multi-specific targeting entities containing at least two different binding entities and uses thereof is reported. Marraffini, L. A., et al. (J. Biol. Chem. 279 (2004) 37763-37770) report for anchoring of surface proteins to the cell wall of *staphylococcus aureus* a conserved arginine residue is required for efficient catalysis of Sortase A.

However, all these approaches have the drawback, that they produce or employ an artificial motive or structure, which may result later on in problems in vivo, like immunogenicity.

SUMMARY OF THE INVENTION

It has been found that the combination of an oligo-alanine as nucleophile with the LPXTG Sortase motif results in suppressed or even completely eliminated back-reaction or hydrolysis of the reaction product as LPXTA is not accepted as substrate.

Thus, one aspect as reported herein is a method for producing an enzymatic conjugation product of two polypeptides comprising the following steps
incubating
  i) a first polypeptide comprising (within the 20 C-terminal amino acid residues) the amino acid sequence LPXTG (SEQ ID NO: 20, wherein X can be any amino acid residue),
  ii) a second polypeptide that has an oligo-alanine $A_m$ (m=2 (SEQ ID NO: 26), or 3 (SEQ ID NO: 27), or 4 (SEQ ID NO: 28), or 5 (SEQ ID NO: 29)) amino acid sequence at its N-terminus,
  iii) a third polypeptide with sortase activity which is derived from *Staphylococcus aureus* Sortase A, and recovering the conjugate from the reaction mixture and thereby producing the enzymatic conjugation product of two polypeptides.

Thus, one aspect as reported herein is a method for producing an enzymatic conjugation product of two polypeptides comprising the following steps incubating i) a first polypeptide comprising (within the 20 C-terminal amino acid residues) the amino acid sequence LPXTG (SEQ ID NO: 20, wherein X can be any amino acid residue), ii) a second polypeptide that comprises i) an alaninyl compound at its N-terminus, or ii) an oligo-alanine $A_m$ (m=2 (SEQ ID NO: 26), or 3 (SEQ ID NO: 27), or 4 (SEQ ID NO: 28), or 5 (SEQ ID NO: 29)), or iii) a cysteine amino acid residue followed by one to three alanine amino acid residues at its N-terminus, iii) a third polypeptide with sortase activity which is derived from *Staphylococcus aureus* Sortase A, and recovering the conjugate from the reaction mixture and thereby producing the enzymatic conjugation product of two polypeptides.

In one embodiment the first polypeptide comprises at its C-terminus the amino acid sequence LPXTG (SEQ ID NO: 20, wherein X can be any amino acid residue).

In one preferred embodiment the first polypeptide comprises at its C-terminus the amino acid sequence LPETG (SEQ ID NO: 30).

In one embodiment the second polypeptide has an oligo-alanine of SEQ ID NO: 26 or SEQ ID NO: 27 at its N-terminus.

In one embodiment the first polypeptide and the second polypeptide are independently of each other selected from an antibody variable domain, an antibody heavy chain Fab-fragment, an antibody Fc-region, a tag, and a peptide comprising the amino acid sequence LPXTG (SEQ ID NO: 20, wherein X can be any amino acid residue), a linker and a non-sortase motif moiety.

In one embodiment the third polypeptide has the amino acid sequence of SEQ ID NO: 21.

One aspect as reported herein is the use of the sortase motif amino acid sequence LPXTG (SEQ ID NO: 20, wherein X can be any amino acid residue) in combination with a peptide comprising an oligo-alanine $A_m$ (m=2 (SEQ ID NO: 26), or 3 (SEQ ID NO: 27), or 4 (SEQ ID NO: 28), or 5 (SEQ ID NO: 29)) amino acid sequence at its N-terminus for increasing the yield of a Sortase catalyzed conjugation reaction between the sortase amino acid sequence and the oligo-alanine comprising peptide.

One aspect as reported herein is the use of the Sortase motif amino acid sequence LPXTG (SEQ ID NO: 20, wherein X can be any amino acid residue) in combination with a peptide comprising an oligo-alanine $A_m$ (m=2 (SEQ ID NO: 26), or 3 (SEQ ID NO: 27), or 4 (SEQ ID NO: 28), or 5 (SEQ ID NO: 29)) amino acid sequence at its N-terminus for reducing by-product formation in a Sortase catalyzed conjugation reaction between the sortase amino acid sequence and the oligo-alanine comprising peptide.

One aspect as reported herein is the use of the sortase motif amino acid sequence LPXTG (SEQ ID NO: 20, wherein X can be any amino acid residue) in combination with a peptide comprising an oligo-alanine $A_m$ (m=2 (SEQ ID NO: 26), or 3 (SEQ ID NO: 27), or 4 (SEQ ID NO: 28), or 5 (SEQ ID NO: 29)) amino acid sequence at its N-terminus for shifting a sortase catalyzed conjugation reaction between the sortase amino acid sequence and the oligo-alanine comprising peptide to the product side.

DETAILED DESCRIPTION OF THE INVENTION

I. Definitions

In the present specification and claims the numbering of the amino acid residues in an immunoglobulin heavy chain Fc-region is that of the EU index of Kabat (Kabat, E. A., et al., Sequences of Proteins of Immunological Interest, 5th ed., Public Health Service, National Institutes of Health, Bethesda, Md. (1991), NIH Publication 91-3242, expressly incorporated herein by reference).

The term "an alaninyl compound" denotes a compound that comprises an alanine amino acid residue with free alpha amino group, e.g. as $NH_2$ or $NH_3^+$, and a carboxy group at position 1 that is in a peptide bond with another moiety, whereby the moiety can be any amino group containing moiety, such as an isolated amino acid residue, a peptide, a polypeptide, a protein, a small molecule, a dye, or a (chemical or peptidic) linker.

The term "comprising" when used herein expressly includes the term "consisting of".

The term "alteration" denotes the mutation, addition, or deletion of one or more amino acid residues in a parent amino acid sequence, e.g. of an antibody or fusion polypeptide comprising at least an FcRn binding portion of an Fc-region, to obtain a variant antibody or fusion polypeptide.

The term "amino acid mutation" denotes a modification in the amino acid sequence of a parent amino acid sequence. Exemplary modifications include amino acid substitutions, insertions, and/or deletions. In one embodiment the amino acid mutation is a substitution. The term "amino acid mutations at the position" denotes the substitution or deletion of the specified residue, or the insertion of at least one amino acid residue adjacent the specified residue. The term "insertion adjacent to a specified residue" denotes the insertion within one to two residues thereof. The insertion may be N-terminal or C-terminal to the specified residue.

The term "amino acid substitution" denotes the replacement of at least one amino acid residue in a predetermined parent amino acid sequence with a different "replacement" amino acid residue. The replacement residue or residues may be a "naturally occurring amino acid residue" (i.e. encoded by the genetic code) and selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); and valine (Val). In one embodiment the replacement residue is not cysteine. Substitution with one or more non-naturally occurring amino acid residues is also encompassed by the definition of an amino acid substitution herein. A "non-naturally occurring amino acid residue" denotes a residue, other than those naturally occurring amino acid residues listed above, which is able to covalently bind adjacent amino acid residues(s) in a polypeptide chain. Examples of non-naturally occurring amino acid residues include norleucine, ornithine, norvaline, homoserine, aib and other amino acid residue analogues such as those described in Ellman, et al., Meth. Enzym. 202 (1991) 301-336. To generate such non-naturally occurring amino acid residues, the procedures of Noren, et al. (Science 244 (1989) 182) and/or Ellman, et al. (supra) can be used. Briefly, these procedures involve chemically activating a suppressor tRNA with a non-naturally occurring amino acid residue followed by in vitro transcription and translation of the RNA. Non-naturally occurring amino acids can also be incorporated into peptides via chemical peptide synthesis and subsequent fusion of these peptides with recombinantly produced polypeptides, such as antibodies or antibody fragments.

The term "amino acid insertion" denotes the incorporation of at least one additional amino acid residue into a predetermined parent amino acid sequence. While the insertion will usually consist of the insertion of one or two amino acid residues, the present application contemplates larger "peptide insertions", e.g. insertion of about three to about five or even up to about ten amino acid residues. The inserted residue(s) may be naturally occurring or non-naturally occurring as defined above.

The term "amino acid deletion" denotes the removal of at least one amino acid residue at a predetermined position in an amino acid sequence.

Within this application whenever an amino acid alteration is mentioned it is a deliberated amino acid alteration and not a random amino acid modification.

The term "tag" denotes a sequence of amino acid residues connected to each other via peptide bonds that has specific binding properties. In one embodiment the tag is an affinity or purification tag. In one embodiment the tag is selected from Arg-tag, His-tag, Flag-tag, 3×Flag-tag, Strep-tag, Nano-tag, SBP-tag, c-myc-tag, S-tag, calmodulin-binding-peptide, cellulose-binding-domain, chitin-binding-domain, GST-tag, or MBP-tag. In one embodiment the tag is selected from SEQ ID NO: 01 (RRRRR), or SEQ ID NO: 02 (RRRRRR), or SEQ ID NO: 03 (HHHHHH), or SEQ ID NO: 04 (KDHLIHNVHKEFHAHAHNK), or SEQ ID NO: 05 (DYKDDDDK), or SEQ ID NO: 06 (DYKDHDGDYKDHDIDYKDDDDK), or SEQ ID NO: 07 (AWRHPQFGG), or SEQ ID NO: 08 (WSHPQFEK), or SEQ ID NO: 09 (MDVEAWLGAR), or SEQ ID NO: 10 (MDVEAWLGARVPLVET), or SEQ ID NO: 11 (MDEKTTGWRGGHVVEGLAGELEQLRARLEHHPQGQREP), or SEQ ID NO: 12 (EQKLISEEDL), or SEQ ID NO: 13 (KETAAAKFERQHMDS), or SEQ ID NO: 14 (KRRWKKNFIAVSAANRF KKISSSGAL), or SEQ ID NO: 15 (cellulose binding domain), or SEQ ID NO: 16 (cellulose binding domain), or SEQ ID NO: 17 (TNPGVSAWQVNTA YTAGQLVTYNGKTYKCLQPHTSLAGWEP SNVPALWQLQ), or SEQ ID NO: 18 (GST-tag), or SEQ ID NO: 19 (MBP-tag).

An "effective amount" of an agent, e.g., a pharmaceutical formulation, refers to an amount effective, at dosages and for periods of time necessary, to achieve the desired therapeutic or prophylactic result.

The term "individual" or "subject" denotes a mammal. Mammals include, but are not limited to, domesticated animals (e.g. cows, sheep, cats, dogs, and horses), primates (e.g., humans and non-human primates such as monkeys), rabbits, and rodents (e.g., mice, rats, and hamsters). In certain embodiments, the individual or subject is a human.

The term "pharmaceutical formulation" refers to a preparation which is in such a form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "position" denotes the location of an amino acid residue in the amino acid sequence of a polypeptide. Positions may be numbered sequentially, or according to an established format, for example the EU index of Kabat for antibody numbering.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

II. Enzymatic Conjugation Using Sortase A

A covalent conjugate comprising two in vivo not covalently associated entities can be obtained in vitro by using the enzyme Sortase, especially Sortase A.

Sortase A (SrtA) is a membrane bound enzyme which attaches proteins covalently to the bacterial cell wall. The specific recognition motif on the SrtA substrate is LPXTG, whereby the enzyme cleaves between the residues threonine and glycine. The recognition motif on the peptidoglycan is a pentaglycine motif. It has been shown that a triglycine and even a diglycine motif on the N-terminus is sufficient to support the SrtA reaction (Clancy, K. W., et al., Peptide science 94 (2010) 385-396). The reaction proceeds through a thioester acyl-enzyme intermediate, which is resolved by the attack of an amine nucleophile from the oligoglycine, covalently linking peptidoglycan to a protein substrate and regenerating SrtA. SrtA can be used to covalently conjugate chemically synthetized peptides to recombinantly expressed proteins.

Many gram-positive bacteria use Sortase to covalently anchor a variety of surface proteins including virulence factors to their cell wall (peptidoglycan). Sortases are membrane associated enzymes. The wild-type *Staphylococcus aureus* Sortase A (SrtA) is a polypeptide of 206 amino acids with an N-terminal membrane-spanning region. In a first step, Sortase A recognizes substrate proteins that contain a LPXTG (SEQ ID NO: 20) amino acid sequence motif and cleaves the amide bond between the Thr and Gly by means of an active-site Cys. This peptide cleaving reaction results in a Sortase A-substrate thioester intermediate. In a second step the thioester acyl-enzyme intermediate is resolved by nucleophilic attack of an amino group of an oligoglycine containing second substrate polypeptide (corresponding to the pentaglycine unit of peptidoglycan in *S. aureus*) leading to a covalently linked cell wall protein and the regeneration of sortase A. In the absence of oligoglycine nucleophiles, the acyl-enzyme intermediate can be hydrolyzed by a water molecule.

Sortase-mediated ligation/conjugation has begun to be applied for a variety of protein engineering and bioconjugation purposes. This technique enables the introduction of natural and synthetic functionalities into LPXTG-tagged recombinant or chemically synthesized polypeptides. Examples include the covalent attachment of oligoglycine derivatized polymers (e.g. PEG), fluorophores, vitamins (e.g. biotin and folate), lipids, carbohydrates, nucleic acids, synthetic peptides and proteins (e.g. GFP) (see e.g. Tsukiji, S. and Nagamune, T., ChemBioChem 10 (2009) 787-798; Popp, M. W. L. and Ploegh, H. L., Angew. Chem. Int. Ed. Engl. 50 (2011) 5024-5032).

For the enzymatic conjugation a soluble truncated Sortase A lacking the membrane-spanning region (SrtA; amino acid residues 60-206 of *Staphylococcus aureus* SrtA) can be used (SEQ ID NO: 21; see also Ton-That, H., et al., Proc. Natl. Acad. Sci. USA 96 (1999) 12424-12429; Ilangovan, H., et al., Proc. Natl. Acad. Sci. USA 98 (2001) 6056-6061).

III. Recombinant Methods

Any polypeptide domain (e.g. a single chain antigen binding polypeptide such as a scFv, a scFab, or a darpin, or a multi chain antigen binding polypeptide such as a dsFv or a Fab) comprising an oligoalanine motif at its N-terminus (AA (SEQ ID NO: 26), AAA (SEQ ID NO: 27), AAAA (SEQ ID NO: 28), AAAAA (SEQ ID NO: 29)) can be expressed and purified from the supernatant of eukaryotic cells (e.g. HEK293 cells, CHO cells). It does not matter if the polypeptide is an isolated polypeptide or comprised in a multimeric or heteromeric entity.

Suitable host cells for cloning or expression/secretion of polypeptide-encoding vectors include prokaryotic or eukaryotic cells described herein. For example, polypeptides may be produced in bacteria, in particular when glycosylation is not needed (see, e.g., U.S. Pat. Nos. 5,648,237, 5,789,199 and 5,840,523, Charlton, Methods in Molecular Biology 248 (2003) 245-254 (B. K. C. Lo, (ed.), Humana Press, Totowa, N.J.), describing expression of antibody fragments in *E. coli.*). After expression, the polypeptide may be isolated from the bacterial cell paste in a soluble fraction or may be isolated from the insoluble fraction so called inclusion bodies which can be solubilized and refolded to bioactive forms. Thereafter the polypeptide can be further purified.

In addition to prokaryotes, eukaryotic microbes such as filamentous fungi or yeasts are suitable cloning or expression hosts for polypeptide-encoding vectors, including fungi and yeast strains whose glycosylation pathways have been "humanized", resulting in the production of a polypeptide with a partially or fully human glycosylation pattern (see e.g. Gerngross, Nat. Biotech. 22 (2004) 1409-1414, and Li, et al., Nat. Biotech. 24 (2006) 210-215).

Suitable host cells for the expression of glycosylated polypeptides are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts (see, e.g., U.S. Pat. Nos. 5,959,177, 6,040,498, 6,420,548, 7,125,978 and 6,417,429 (describing PLANTIBODIES™ technology for producing antibodies in transgenic plants)).

Vertebrate cells may also be used as hosts. For example, mammalian cell lines that are adapted to grow in suspension may be useful. Other examples of useful mammalian host cell lines are the COS-7 cell line (monkey kidney CV1 cell transformed by SV40); the HEK293 cell line (human embryonic kidney); the BHK cell line (baby hamster kidney); the TM4 mouse sertoli cell line (TM4 cells as described, e.g., in Mather, Biol. Reprod. 23 (1980) 243-251); the CV1 cell line (monkey kidney cell); the VERO-76 cell line (African green monkey kidney cell); the HELA cell line (human cervical carcinoma cell); the MDCK cell line (canine kidney cell); the BRL-3A cell line (buffalo rat liver cell); the W138 cell line (human lung cell); the HepG2 cell line (human liver cell); the MMT 060562 cell line (mouse mammary tumor cell); the TRI cell line (e.g. described in Mather, et al., Anal. N.Y. Acad. Sci. 383 (1982) 44-68); the MRCS cell line; and the FS4 cells-line. Other useful mammalian host cell lines include the CHO cell line (Chinese hamster ovary cell), including DHFR negative CHO cell lines (see e.g. Urlaub, et al., Proc. Natl. Acad. Sci. USA 77 (1980) 4216), and myeloma cell lines such as YO, NSO and Sp2/0 cell line. For a review of certain mammalian host cell lines suitable for polypeptide production, see, e.g., Yazaki, and Wu, Methods in Molecular Biology, Antibody Engineering 248 (2004) 255-268 (B. K. C. Lo, (ed.), Humana Press, Totowa, N.J.).

IV. The Method as Reported Herein

Sortase mediated polypeptide conjugation reactions generally have the drawback that the reaction equilibrium is not on the product side. Thus, it is beneficial to either shift the equilibrium or to remove the product. In the Table below the relative activity of Sortase (*Staphylococcus aureus*) with different substrates is shown.

TABLE

|  |  | Sortase motif | |
|---|---|---|---|
|  |  | LPXTG | LPXTA |
| nucleophile (in excess) | oligoglycine | 100% | 0% |
|  | oligoalanine | 5% | 0% |

Thus, it has been found that the combination of an oligo-alanine as nucleophile with the LPXTG sortase motif results in suppressed or even completely eliminated back-reaction or hydrolysis of the reaction product as LPXTA is not accepted as substrate (see FIGS. 1, 3 and 4).

This has been exemplified using two antibody Fc-region fragments in a Sortase mediated ligation reaction. One Fc-region fragment comprises a C-terminal LPETG Sortase motif whereas the other Fc-region fragment comprises an N-terminal oligo-alanine (AAA, SEQ ID NO: 27) as nucleophile. Samples of the reaction mixture were analyzed after 16 hours and 40 hours (see FIG. 2). It can be seen that the desired ligation product (Fc-region dimer, approx. 60 kDa) is formed after 16 hours. Even after 40 hours incubation time no hydrolysis of the formed product occurred, despite the high concentration of Sortase (1:10 ratio enzyme:substrate).

In case of LPETG and oligo-glycine (GGG, SEQ ID NO: 23) a decomposition of the formed sortase product was observed.

With this combination of reagents
i) the reverse reaction recognizing the LPXTG amino acid sequence within the product conjugate as substrate, and/or
ii) the generation of a dead-end hydrolysis polypeptide fragment (polypeptide with without/cleaved LPXTG recognition sequence generated through cleavage of the thioacyl-binding entity Sortase A intermediate by water instead by the Fc-region nucleophile)
that is normally occurring at increased reaction times can be reduced or even eliminated.

Non-Sortase Motif Moiety

The Sortase motif amino acid sequence LPXTG may be conjugated, if it is not directly comprises in one of these molecules, to a therapeutic agent (drug), a cytotoxic agent (e.g. a toxin such as doxorubicin or pertussis toxin), a fluorophores such as a fluorescent dye like fluorescein or rhodamine, a chelating agent for an imaging or radiotherapeutic metal, a peptidyl or non-peptidyl label, a tag, or a clearance-modifying agent such as various isomers of polyethylene glycol, a peptide that binds to a third component, or another carbohydrate or lipophilic agent. The conjugation can be either directly or via an intervening linker.

a) Therapeutic Moieties

The drug moiety can be any compound, moiety or group which has a therapeutic effect, such as an antibody, a cytotoxic or cytostatic compound.

A number of therapeutic antibodies directed against cell surface molecules and their ligands are known, such as Rituxan/MabThera/Rituximab, 2H7/Ocrelizumab, Zevalin/Ibrizumomab, Arzerra/Ofatumumab (CD20), HLL2/Epratuzumab, Inotuzumab (CD22), Zenapax/Daclizumab, Simulect/Basiliximab (CD25), Herceptin/Trastuzumab, Pertuzumab (Her2/ERBB2), Mylotarg/Gemtuzumab (CD33), Raptiva/Efalizumab (Cd11a), Erbitux/Cetuximab (EGFR, epidermal growth factor receptor), IMC-1121B (VEGF receptor 2), Tysabri/Natalizumab (α4-subunit of α4β1 and α4β7 integrins), ReoPro/Abciximab (gpIIb-gpIIa and αvβ3-integrin), Orthoclone OKT3/Muromonab-CD3 (CD3), Benlysta/Belimumab (BAFF), Tolerx/Oteliximab (CD3), Soliris/Eculizumab (C5 complement protein), Actemra/Tocilizumab (IL-6R), Panorex/Edrecolomab (EpCAM, epithelial cell adhesion molecule), CEA-CAMS/Labetuzumab (CD66/CEA, carcinoembryonic antigen), CT-11 (PD-1, programmed death-1 T-cell inhibitory receptor, CD-d279), H224G11 (c-Met receptor), SAR3419 (CD19), IMC-A12/Cixutumumab (IGF-1R, insulin-like growth factor 1 receptor), MEDI-575 (PDGF-R, platelet-derived growth factor receptor), CP-675, 206/Tremelimumab (cytotoxic T lymphocyte antigen 4), RO5323441 (placenta growth factor or PGF), HGS1012/Mapatumumab (TRAIL-R1), SGN-70 (CD70), Vedotin (SGN-35)/Brentuximab (CD30), and ARH460-16-2 (CD44).

The conjugates obtained with the method as reported herein can be used in the preparation of medicaments for the treatment of e.g. an oncologic disease, a cardiovascular disease, an infectious disease, an inflammatory disease, an autoimmune disease, a metabolic (e.g., endocrine) disease, or a neurological (e.g. neurodegenerative) disease. Exemplary non-limiting examples of these diseases are Alzheimer's disease, non-Hodgkin's lymphomas, B-cell acute and chronic lymphoid leukemias, Burkitt lymphoma, Hodgkin's lymphoma, hairy cell leukemia, acute and chronic myeloid leukemias, T-cell lymphomas and leukemias, multiple myeloma, glioma, Waldenstrom's macroglobulinemia, carcinomas (such as carcinomas of the oral cavity, gastrointestinal tract, colon, stomach, pulmonary tract, lung, breast, ovary, prostate, uterus, endometrium, cervix, urinary bladder, pancreas, bone, liver, gall bladder, kidney, skin, and testes), melanomas, sarcomas, gliomas, and skin cancers, acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjogren's syndrome, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis, or fibrosing alveolitis.

A number of cell surface markers and their ligands are known. For example cancer cells have been reported to express at least one of the following cell surface markers and or ligands, including but not limited to, carbonic anhydrase IX, alpha-fetoprotein, alpha-actinin-4, A3 (antigen specific for A33 antibody), ART-4, B7, Ba-733, BAGE, BrE3-antigen, CA125, CAMEL, CAP-1, CASP-8/m, CCCL19, CCCL21, CD1, CD1a, CD2, CD3, CD4, CDS, CD8, CD1-1A, CD14, CD15, CD16, CD18, CD19, CD20, CD21, CD22, CD23, CD25, CD29, CD30, CD32b, CD33, CD37, CD38, CD40, CD40L, CD45, CD46, CD54, CD55, CD59, CD64, CD66a-e, CD67, CD70, CD74, CD79a, CD80, CD83, CD95, CD126, CD133, CD138, CD147, CD154, CDC27, CDK-4/m, CDKN2A, CXCR4, CXCR7, CXCL12, HIF-1-alpha, colon-specific antigen-p (CSAp), CEA (CEACAMS), CEACAM6, c-met, DAM, EGFR, EGFRvIII, EGP-1, EGP-2, ELF2-M, Ep-CAM, Flt-1, Flt-3, folate receptor, G250 antigen, GAGE, GROB, HLA-DR, HM1.24, human chorionic gonadotropin (HCG) and its subunits, HER2/neu, HMGB-1, hypoxia inducible factor (HIF-1), HSP70-2M, HST-2 or 1a, IGF-1R, IFN-gamma, IFN-alpha, IFN-beta, IL-2, IL-4R, IL-6R, IL-13R, IL-15R, IL-17R, IL-18R, IL-6, IL-8, IL-12, IL-15, IL-17, IL-18, IL-25, insulin-like growth factor-1 (IGF-1), KC4-antigen, KS-1-antigen, KS1-4, Le-Y, LDR/FUT, macrophage migration inhibitory factor (MIF), MAGE, MAGE-3, MART-1, MART-2, NY-ESO-1, TRAG-3, mCRP, MCP-1, MIP-1A, MIP-1B, MIF, MUC1, MUC2, MUC3, MUC4, MUC5, MUM-1/2, MUM-3, NCA66, NCA95, NCA90, pancreatic cancer mucin, placental growth factor, p53, PLAGL2, prostatic acid phosphatase, PSA, PRAME, PSMA, P1GF, ILGF, ILGF-1R, IL-6, IL-25, RSS, RANTES, T101, SAGE, 5100, survivin, survivin-2B, TAC, TAG-72, tenascin, TRAIL receptors, TNF-alpha, Tn-antigen, Thomson-Friedenreich antigens, tumor necrosis antigens, VEGFR, ED-B fibronectin, WT-1, 17-1A-antigen, complement factors C3, C3a, C3b, C5a, C5, an angiogenesis marker, bcl-2, bcl-6, Kras, cMET, an oncogene marker and an oncogene product (see, e.g., Sensi, et al., Clin. Cancer Res. 12 (2006) 5023-5032; Parmiani, et al, J. Immunol. 178 (2007) 1975-1979; Novellino, et al., Cancer Immunol. Immunother. 54 (2005) 187-207).

Thus, antibodies recognizing specific cell surface receptors including their ligands can be used for specific and selective targeting and binding to a number/multitude of cell surface markers that are associated with a disease. A cell surface marker is a polypeptide located on the surface of a cell (e.g. a disease-related cell) that is e.g. associated with signaling event or ligand binding.

In one embodiment, for the treatment of cancer/tumors multispecific binding molecules/bispecific antibodies are produced that target tumor-associated antigens, such as those reported in Herberman, "Immunodiagnosis of Cancer", in Fleisher (ed.), "The Clinical Biochemistry of Cancer", page 347 (American Association of Clinical Chemists (1979)) and in U.S. Pat. Nos. 4,150,149; 4,361,544; and 4,444,744.

Reports on tumor associated antigens (TAAs) include Mizukami, et al., (Nature Med. 11 (2005) 992-997); Hatfield, et al., (Curr. Cancer Drug Targets 5 (2005) 229-248); Vallbohmer, et al., (J Clin. Oncol. 23 (2005) 3536-3544);

and Ren, et al., (Ann. Surg. 242 (2005) 55-63), each incorporated herein by reference with respect to the TAAs identified.

Where the disease involves a lymphoma, leukemia or autoimmune disorder, targeted antigens may be selected from the group consisting of CD4, CD5, CD8, CD14, CD15, CD19, CD20, CD21, CD22, CD23, CD25, CD33, CD37, CD38, CD40, CD40L, CD46, CD54, CD67, CD74, CD79a, CD80, CD126, CD138, CD154, CXCR4, B7, MUC1 or 1a, HM1.24, HLA-DR, tenascin, VEGF, P1GF, ED-B fibronectin, an oncogene, an oncogene product (e.g., c-met or PLAGL2), CD66a-d, necrosis antigens, IL-2, T101, TAG, IL-6, MIF, TRAIL-R1 (DR4) and TRAIL-R2 (DR5).

A number of bispecific antibodies are known directed against two different targets, such as BCMA/CD3, different antigens of the HER family in combination (EGFR, HER2, HER3), CD19/CD3, IL17RA/IL7R, IL-6/IL-23, IL-1-beta/IL-8, IL-6 or IL-6R/IL-21 or IL-21R, first specificity directed to a glycoepitope of an antigen selected from the group consisting of Lewis x-, Lewis b- and Lewis y-structures, Globo H-structures, KH1, Tn-antigen, TF-antigen and carbohydrate structures of Mucins, CD44, glycolipids and glycosphingolipids, such as Gg3, Gb3, GD3, GD2, Gb5, Gm1, Gm2, sialyltetraosylceramide and a second specificity directed to an ErbB receptor tyrosine kinase selected from the group consisting of EGFR, HER2, HER3 and HER4, GD2 in combination with a second antigen binding site is associated with an immunological cell chosen from the group consisting of T-lymphocytes NK cell, B-lymphocytes, dendritic cells, monocytes, macrophages, neutrophils, mesenchymal stem cells, neural stem cells, ANG2/VEGF, VEGF/PDGFR-beta, Vascular Endothelial Growth Factor (VEGF) acceptor 2/CD3, PSMA/CD3, EPCAM/CD3, combinations of an antigen is selected from a group consisting of VEGFR-1, VEGFR-2, VEGFR-3, FLT3, c-FMS/CSF1R, RET, c-Met, EGFR, Her2/neu, HER3, HER4, IGFR, PDGFR, c-KIT, BCR, integrin and MMPs with a water-soluble ligand is selected from the group consisting of VEGF, EGF, PlGF, PDGF, HGF, and angiopoietin, ERBB-3/C-MET, ERBB-2/C-MET, EGF receptor 1/CD3, EGFR/HER3, PSCA/CD3, C-MET/CD3, ENDOSIALIN/CD3, EPCAM/CD3, IGF-1R/CD3, FAPALPHA/CD3, EGFR/IGF-1R, IL 17A/F, EGF receptor 1/CD3, and CD19/CD16.

Toxic drug moieties include: (i) chemotherapeutic agents, which may function as microtubule inhibitors, mitosis inhibitors, topoisomerase inhibitors, or DNA intercalators; (ii) protein toxins, which may function enzymatically; and (iii) radioisotopes.

Exemplary toxic drug moieties include, but are not limited to, a maytansinoid, an auristatin, a dolastatin, a trichothecene, CC1065, a calicheamicin and other enediyne antibiotics, a taxane, an anthracycline, and stereoisomers, isosters, analogs or derivatives thereof.

Protein toxins include diphtheria-A chain, non-binding active fragments of diphtheria toxin, exotoxin A chain (from *Pseudomonas aeruginosa*), ricin A chain (Vitetta et al (1987) Science, 238:1098), abrin A chain, modeccin A chain, alpha-sarcin, *Aleurites fordii* proteins, dianthin proteins, *Phytolaca americana* proteins (PAPI, PAPII, and PAP-5), *momordica charantia* inhibitor, curcin, crotin, *sapaonaria officinalis* inhibitor, gelonin, mitogellin, restrictocin, phenomycin, enomycin, and the tricothecenes (WO 93/21232).

Therapeutic radioisotopes include 32P, 33P, 90Y, 125I, 131I, 131In, 153Sm, 186Re, 188Re, 211At, 212B, 212Pb, and radioactive isotopes of Lu.

The radioisotope or other labels may be incorporated in known ways (Fraker et al (1978) Biochem. Biophys. Res. Commun. 80: 49-57; "Monoclonal Antibodies in Immunoscintigraphy" Chatal, CRC Press 1989). Carbon-14-labeled 1-isothiocyanatobenzyl-3-methyldiethylene triamine pentaacetic acid (MX-DTPA) is an exemplary chelating agent for conjugation of a radionuclide to the complex (WO 94/11026).

b) Labels

The non-Sortase motif moiety can be a label. Any label moiety which can be covalently attached to the sortase amino acid sequence can be used (see e.g. Singh et al (2002) Anal. Biochem. 304:147-15; Harlow E. and Lane, D. (1999) Using Antibodies: A Laboratory Manual, Cold Springs Harbor Laboratory Press, Cold Spring Harbor, N.Y.; Lundblad R. L. (1991) Chemical Reagents for Protein Modification, 2nd ed. CRC Press, Boca Raton, Fla.). The label may function to: (i) provide a detectable signal; (ii) interact with a second label to modify the detectable signal provided by the first or second label, e.g. to give FRET (fluorescence resonance energy transfer); (iii) affect mobility, e.g. electrophoretic mobility or cell-permeability, by charge, hydrophobicity, shape, or other physical parameters, or (iv) provide a capture moiety, e.g. to modulate ionic complexation.

Conjugates comprising a haptenylated label as reported herein may be useful in diagnostic assays, e.g., for detecting expression of an antigen of interest in specific cells, tissues, or serum. For diagnostic applications, a bispecific antibody will be used wherein the first binding specificity binds to a target and the second binding specificity binds to a haptenylated label. The hapten will typically be labeled with a detectable moiety. Numerous labels are available which can be generally grouped into the following categories:

(a) Radioisotopes (radionuclides), such as 3H, 11C, 14C, 18F, 32P, 35S, 64Cu, 68Gn, 86Y, 89Zr, 99TC, 111In, 123I, 124I, 125I, 131I, 133Xe, 177Lu, 211At, or 131Bi. Radioisotope labeled conjugates are useful in receptor targeted imaging experiments. The antigen (hapten) can be labeled with ligand reagents that bind, chelate or otherwise complex a radioisotope metal using the techniques described in Current Protocols in Immunology, (1991) Volumes 1 and 2, Coligen et al, Ed. Wiley-Interscience, New York, N.Y., Pubs. Chelating ligands which may complex a metal ion include DOTA, DOTP, DOTMA, DTPA and TETA (Macrocyclics, Dallas, Tex.). Radionuclides can be targeted via complexation with the complex as reported herein (Wu et al, Nature Biotechnology 23(9) (2005) 1137-1146). Receptor target imaging with radionuclide labeled complexes can provide a marker of pathway activation by detection and quantification of progressive accumulation of complexes or corresponding therapeutic antibodies in tumor tissue (Albert et al (1998) Bioorg. Med. Chem. Lett. 8:1207-1210).

Metal-chelate complexes suitable as labels for imaging experiments (US 2010/0111856; U.S. Pat. Nos. 5,342,606; 5,428,155; 5,316,757; 5,480,990; 5,462,725; 5,428,139; 5,385,893; 5,739,294; 5,750,660; 5,834,456; Hnatowich et al, J. Immunol. Methods 65 (1983) 147-157; Meares et al, Anal. Biochem. 142 (1984) 68-78; Mirzadeh et al, Bioconjugate Chem. 1 (1990) 59-65; Meares et al, J. Cancer (1990), Suppl. 10:21-26; Izard et al, Bioconjugate Chem. 3 (1992) 346-350; Nikula et al, Nucl. Med. Biol. 22 (1995) 387-90; Camera et al, Nucl. Med. Biol. 20 (1993) 955-62; Kukis et al, J. Nucl. Med. 39 (1998) 2105-2110; Verel et al., J. Nucl. Med. 44 (2003) 1663-1670; Camera et al, J. Nucl. Med. 21 (1994) 640-646; Ruegg et al, Cancer Res. 50 (1990) 4221-4226; Verel et al, J. Nucl. Med. 44 (2003) 1663-1670; Lee et al, Cancer Res. 61 (2001) 4474-4482; Mitchell, et al, J. Nucl. Med. 44 (2003) 1105-1112; Kobayashi et al Bioconjugate Chem. 10 (1999) 103-111; Miederer et al, J. Nucl.

Med. 45 (2004) 129-137; DeNardo et al, Clinical Cancer Research 4 (1998) 2483-90; Blend et al, Cancer Biotherapy & Radiopharmaceuticals 18 (2003) 355-363; Nikula et al J. Nucl. Med. 40 (1999) 166-76; Kobayashi et al, J. Nucl. Med. 39 (1998) 829-36; Mardirossian et al, Nucl. Med. Biol. 20 (1993) 65-74; Roselli et al, Cancer Biotherapy & Radiopharmaceuticals, 14 (1999) 209-20).

(b) Fluorescent labels such as rare earth chelates (europium chelates), fluorescein types including FITC, 5-carboxyfluorescein, 6-carboxy fluorescein; rhodamine types including TAMRA; dansyl; Lissamine; cyanines; phycoerythrins; Texas Red; and analogs thereof. The fluorescent labels can be conjugated to the antigen (hapten) using the techniques disclosed in Current Protocols in Immunology, supra, for example. Fluorescent dyes and fluorescent label reagents include those which are commercially available from Invitrogen/Molecular Probes (Eugene, Oreg., USA) and Pierce Biotechnology, Inc. (Rockford, Ill.).

Detection labels such as fluorescent dyes and chemiluminescent dyes (Briggs et al "Synthesis of Functionalised Fluorescent Dyes and Their Coupling to Amines and Amino Acids," J. Chem. Soc., Perkin-Trans. 1 (1997) 1051-1058) provide a detectable signal and are generally applicable for labeling, especially with the following properties: (i) the labeled conjugate should produce a very high signal with low background so that small quantities of conjugate can be sensitively detected in both cell-free and cell-based assays; and (ii) the labeled conjugate should be photostable so that the fluorescent signal may be observed, monitored and recorded without significant photo bleaching. For applications involving cell surface binding of labeled conjugates to membranes or cell surfaces, especially live cells, the labels should (iii) have good water-solubility to achieve effective conjugate concentration and detection sensitivity and (iv) are non-toxic to living cells so as not to disrupt the normal metabolic processes of the cells or cause premature cell death.

(c) Various enzyme-substrate labels are available or disclosed (see e.g. U.S. Pat. No. 4,275,149). The enzyme generally catalyzes a chemical alteration of a chromogenic substrate that can be measured using various techniques. For example, the enzyme may catalyze a color change in a substrate, which can be measured spectrophotometrically. Alternatively, the enzyme may alter the fluorescence or chemiluminescence of the substrate. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRP), alkaline phosphatase (AP), (3-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to polypeptides are described in O'Sullivan et al "Methods for the Preparation of Enzyme-Antibody Conjugates for use in Enzyme Immunoassay", in Methods in Enzym. (ed. by J. Langone & I T Van Vunakis), Academic Press, New York, 73 (1981) 147-166.

Examples of enzyme-substrate combinations (U.S. Pat. Nos. 4,275,149; 4,318,980) include, for example:
(i) Horseradish peroxidase (HRP) with hydrogen peroxidase as a substrate, wherein the hydrogen peroxidase oxidizes a dye precursor (e.g., orthophenylene diamine (OPD) or 3,3',5,5'-tetramethylbenzidine hydrochloride (TMB));
(ii) alkaline phosphatase (AP) with para-nitrophenyl phosphate as chromogenic substrate; and
(iii) (3-D-galactosidase ((3-D-Gal) with a chromogenic substrate (e.g., p-nitro phenyl-(3-D-galactosidase) or fluorogenic substrate 4-methylumbelliferyl-(3-D-galactosidase.

The labeled conjugate as reported herein may be employed in any known assay method, such as ELISA, competitive binding assays, direct and indirect sandwich assays, and immunoprecipitation assays (Zola, Monoclonal Antibodies: A Manual of Techniques (1987) pp. 147-158, CRC Press, Inc.).

Labeled conjugates as reported herein are useful as imaging biomarkers and probes by the various methods and techniques of biomedical and molecular imaging such as: (i) MRI (magnetic resonance imaging); (ii) MicroCT (computerized tomography); (iii) SPECT (single photon emission computed tomography); (iv) PET (positron emission tomography) Tinianow, J. et al, Nuclear Medicine and Biology, 37(3) (2010) 289-297; Chen et al, Bioconjugate Chem. 15 (2004) 41-49; US 2010/0111856 (v) bioluminescence; (vi) fluorescence; and (vii) ultrasound. Immunoscintigraphy is an imaging procedure in which conjugates labeled with radioactive substances are administered to an animal or human patient and a picture is taken of sites in the body where the conjugate localizes (U.S. Pat. No. 6,528,624). Imaging biomarkers may be objectively measured and evaluated as an indicator of normal biological processes, pathogenic processes, or pharmacological responses to a therapeutic intervention. Biomarkers may be of several types: Type 0 markers are natural history markers of a disease and correlate longitudinally with known clinical indices, e.g. MRI assessment of synovial inflammation in rheumatoid arthritis; Type I markers capture the effect of an intervention in accordance with a mechanism-of-action, even though the mechanism may not be associated with clinical outcome; Type II markers function as surrogate endpoints where the change in, or signal from, the biomarker predicts a clinical benefit to "validate" the targeted response, such as measured bone erosion in rheumatoid arthritis by CT. Imaging biomarkers thus can provide pharmacodynamic (PD) therapeutic information about: (i) expression of a target protein, (ii) binding of a therapeutic to the target protein, i.e. selectivity, and (iii) clearance and half-life pharmacokinetic data. Advantages of in vivo imaging biomarkers relative to lab-based biomarkers include: non-invasive treatment, quantifiable, whole body assessment, repetitive dosing and assessment, i.e. multiple time points, and potentially transferable effects from preclinical (small animal) to clinical (human) results. For some applications, bioimaging supplants or minimizes the number of animal experiments in preclinical studies.

Peptide labeling methods are well known. See Haugland (2003) Molecular Probes Handbook of Fluorescent Probes and Research Chemicals, Molecular Probes, Inc.; Brinkley (1992) Bioconjugate Chem. 3:2; Garman, (1997) Non-Radioactive Labeling: A Practical Approach, Academic Press, London; Means (1990) Bioconjugate Chem. 1:2; Glazer et al Chemical Modification of Proteins. Laboratory Techniques in Biochemistry and Molecular Biology (T. S. Work and E. Work, Eds.) American Elsevier Publishing Co., New York; Lundblad, R. L. and Noyes, C. M. (1984) Chemical Reagents for Protein Modification, Vols. I and II, CRC Press, New York; Pfleiderer, G. (1985) "Chemical Modification of Proteins", Modern Methods in Protein Chemistry, H. Tschesche, Ed., Walter DeGruyter, Berlin and New York; and Wong (1991) Chemistry of Protein Conjugation and Cross-linking, CRC Press, Boca Raton, Fla.); DeLeon-Rodriguez et al, Chem. Eur. J. 10 (2004) 1149-1155; Lewis et al, Bioconjugate Chem. 12 (2001) 320-324; Li et al, Bioconjugate Chem. 13 (2002) 110-115; Mier et al Bioconjugate Chem. 16 (2005) 240-237.

Linker

The term "linker" denotes a bifunctional or multifunctional moiety which can be used to conjugate (link) a first moiety with a second moiety. Linked conjugates can be conveniently prepared using a linker having two reactive functionalities.

In one embodiment, a linker has a reactive site which has an electrophilic group that is reactive to a nucleophilic group present in the sortase amino acid sequence. Useful electrophilic groups include, but are not limited to, another thiol, maleimide and haloacetamide groups (see e.g. conjugation method at page 766 of Klussman et al, Bioconjugate Chemistry 15(4) (2004) 765-773).

Examples of thiol-reaction functional groups include, but are not limited to, thiol, maleimide, alpha-haloacetyl, activated esters such as succinimide esters, 4-nitrophenyl esters, pentafluorophenyl esters, tetrafluorophenyl esters, anhydrides, acid chlorides, sulfonyl chlorides, isocyanates and isothiocyanates.

The linker may comprise amino acid residues which link the sortase amino acid sequence to the non-sortase motif moiety. The amino acid residues may form a dipeptide, tripeptide, tetrapeptide, pentapeptide, hexapeptide, heptapeptide, octapeptide, nonapeptide, decapeptide, undecapeptide or dodecapeptide unit. Amino acid residues include those occurring naturally, as well as non-naturally occurring amino acid analogs, such as e.g. citrulline or β-amino acids, such as e.g. β-alanine, or ω-amino acids such as 4-aminobutyric acid.

In another embodiment, the linker has a reactive functional group which has a nucleophilic group that is reactive to an electrophilic group present in the sortase amino acid sequence. Useful electrophilic groups include, but are not limited to, aldehyde and ketone carbonyl groups. The heteroatom of a nucleophilic group of a linker can react with an electrophilic group in the sortase amino acid sequence and form a covalent bond to the sortase amino acid sequence. Useful nucleophilic groups on a linker include, but are not limited to, hydrazide, oxime, amino, hydrazine, thiosemicarbazone, hydrazine carboxylate, and arylhydrazide. The electrophilic group on an antigen (hapten) provides a convenient site for attachment to a linker.

Typically, peptide-type linkers can be prepared by forming a peptide bond between two or more amino acids and/or peptide fragments. Such peptide bonds can be prepared, for example, according to the liquid phase synthesis method (E. Schroder and K. Lubke "The Peptides", volume 1 (1965) 76-136, Academic Press) which is well known in the field of peptide chemistry.

In another embodiment, the linker may be substituted with groups which modulated solubility or reactivity. For example, a charged substituent such as sulfonate ($SO_3^-$) or ammonium or a polymer such as PEG, may increase water solubility of the reagent and facilitate the coupling reaction of the linker reagent with the antigen (hapten) or the drug moiety, or facilitate the coupling reaction depending on the synthetic route employed.

The conjugates comprising a non-sortase motif moiety as reported herein expressly contemplate, but are not limited to, complexes prepared with linker reagents: BMPEO, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone) benzoate), and including bis-maleimide reagents: DTME, BMB, BMDB, BMH, BMOE, BM(PEO)$_3$, and BM(PEO)$_4$, which are commercially available from Pierce Biotechnology, Inc. Bis-maleimide reagents allow the attachment of e.g. a thiol group to a thiol-containing drug moiety, label, or linker intermediate, in a sequential or concurrent fashion. Other functional groups besides maleimide, which are reactive with e.g. a thiol group, include iodoacetamide, bromoacetamide, vinyl pyridine, disulfide, pyridyl disulfide, isocyanate, and isothiocyanate.

Exemplary linker include a valine-citrulline (val-cit or vc) dipeptide linker reagent having a maleimide stretcher and a para-aminobenzylcarbamoyl (PAB) self-immolative spacer, and a phe-lys (Mtr) dipeptide linker reagent having a maleimide Stretcher unit and a p-amino benzyl self-immolative spacer.

Cysteine thiol groups are nucleophilic and capable of reacting to form covalent bonds with electrophilic groups on linker reagents and the non-sortase motif moiety or the sortase amino acid sequence including: (i) active esters such as NHS esters, HOBt esters, haloformates, and acid halides; (ii) alkyl and benzyl halides, such as haloacetamides; (iii) aldehydes, ketones, carboxyl, and maleimide groups; and (iv) disulfides, including pyridyl disulfides, via sulfide exchange. Nucleophilic groups on a haptenylated compound include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents.

Figure 1:
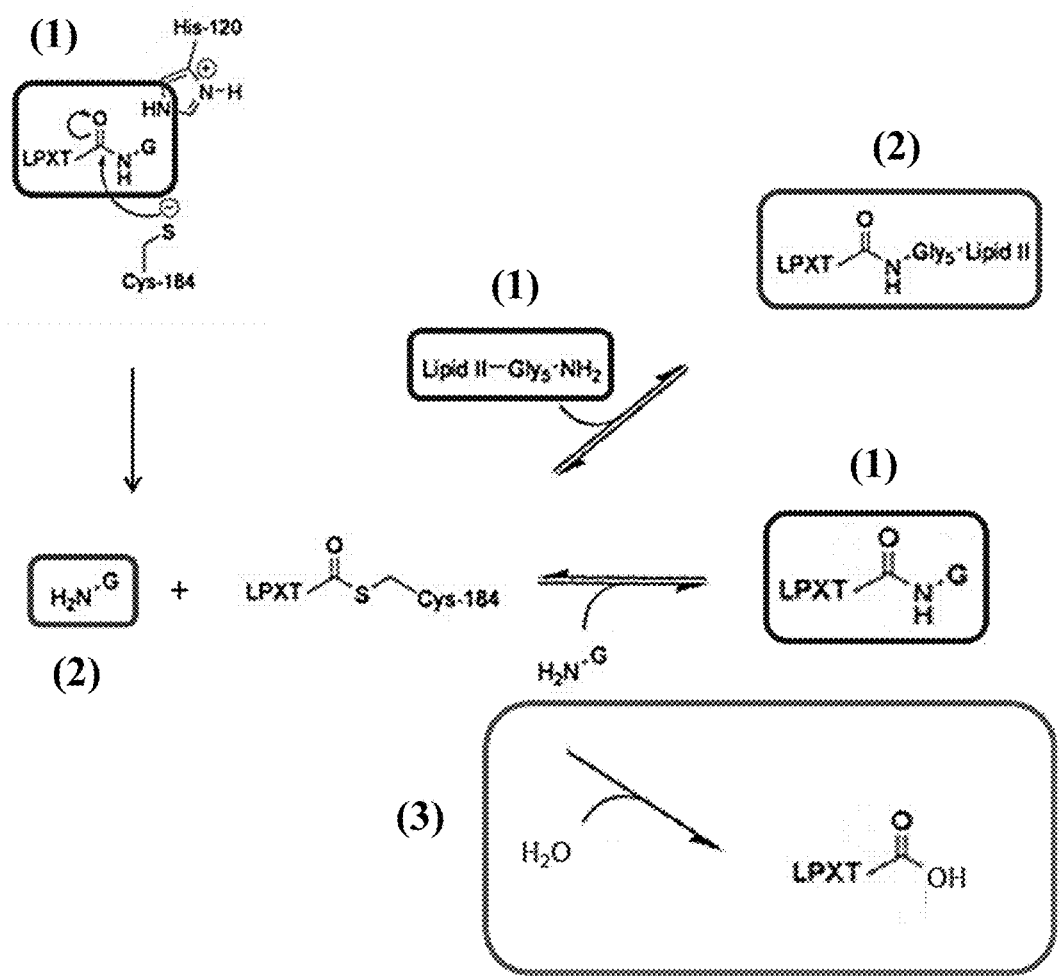
FIG. 1 Sortase reaction scheme; (1) educts, (2) products, (3) hydrolysis (side-reaction leading to by-products).
Figure 2:
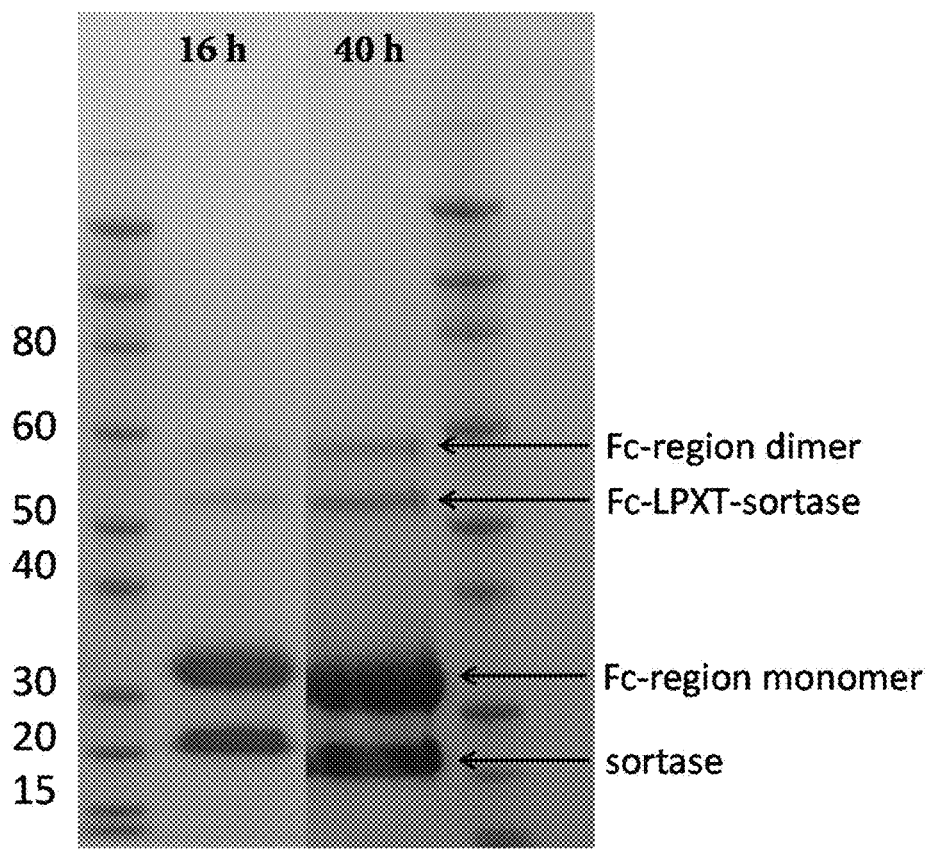
FIG. 2 SDS-page gel of the enzymatic reaction mixture after 16 hours and 40 hours.

The following examples, figures and sequences are provided to aid the understanding of the present invention, the true scope of which is set forth in the appended claims. It is understood that modifications can be made in the procedures set forth without departing from the spirit of the invention.

Although the foregoing invention has been described in some detail by way of illustration and example for purposes of clarity of understanding, the descriptions and examples should not be construed as limiting the scope of the invention.

EXAMPLES

Recombinant DNA Techniques

Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions.

Gene and Oligonucleotide Synthesis

Desired gene segments were prepared by chemical synthesis at Geneart GmbH (Regensburg, Germany). The synthesized gene fragments were cloned into an *E. coli* plasmid for propagation/amplification. The DNA sequences of subcloned gene fragments were verified by DNA sequencing. Alternatively, short synthetic DNA fragments were assembled by annealing chemically synthesized oligonucleotides or via PCR. The respective oligonucleotides were prepared by metabion GmbH (Planegg-Martinsried, Germany).

Description of the Basic/Standard Mammalian Expression Plasmid

For the expression of a desired gene/protein (e.g. full length antibody heavy chain, full length antibody light chain, or an Fc-chain containing an oligoglycine at its N-terminus) a transcription unit comprising the following functional elements is used:
- the immediate early enhancer and promoter from the human cytomegalovirus (P-CMV) including intron A,
- a human heavy chain immunoglobulin 5'-untranslated region (5'UTR),
- a murine immunoglobulin heavy chain signal sequence,
- a gene/protein to be expressed (e.g. full length antibody heavy chain), and
- the bovine growth hormone polyadenylation sequence (BGH pA).

Beside the expression unit/cassette including the desired gene to be expressed the basic/standard mammalian expression plasmid contains
- an origin of replication from the vector pUC18 which allows replication of this plasmid in *E. coli*, and
- a beta-lactamase gene which confers ampicillin resistance in *E. coli*.

Protein Determination

The protein concentration of purified polypeptides was determined by determining the optical density (OD) at 280 nm, using the molar extinction coefficient calculated on the basis of the amino acid sequence of the polypeptide.

Example 1

Generation of an Expression Plasmid for Soluble *S. aureus* Sortase A

The sortase gene encodes an N-terminally truncated Sortase A (60-206) molecule (amino acid sequence of SEQ ID NO: 21).

The expression plasmid for the transient expression of soluble Sortase in HEK293 cells comprised besides the soluble Sortase expression cassette an origin of replication from the vector pUC18, which allows replication of this plasmid in *E. coli*, and a beta-lactamase gene which confers ampicillin resistance in *E. coli*.

The transcription unit of the soluble Sortase comprised the following functional elements:
- the immediate early enhancer and promoter from the human cytomegalovirus (P-CMV) including intron A,
- a human heavy chain immunoglobulin 5'-untranslated region (5'UTR),
- a murine immunoglobulin heavy chain signal sequence,
- a purification tag encoding nucleic acid,
- an N-terminally truncated *S. aureus* Sortase A encoding nucleic acid, and
- the bovine growth hormone polyadenylation sequence (BGH pA).

The amino acid sequence of the mature soluble Sortase is

```
                                           (SEQ ID NO: 21)
QAKPQIPKDKSKVAGYIEIPDADIKEPVYPGPATPEQLNRGVSFAEENES

LDDQNISIAGHTFIDRPNYQFTNLKAAKKGSMVYFKVGNETRKYKMTSIR

DVKPTDVGVLDEQKGKDKQLTLITCDDYNEKTGVWEKRKIFVATEVK.
```

The purification tag has the amino acid sequence MRG-SHHHHHHGS (SEQ ID NO: 31).

Example 2

Transient Expression and Analytical Characterization

The recombinant production was performed by transient transfection of HEK293 cells (human embryonic kidney cell line 293-derived) cultivated in F17 Medium (Invitrogen Corp.). For transfection "293-Fectin" Transfection Reagent (Invitrogen) was used. Transfection was performed as specified in the manufacturer's instructions. Cell culture supernatants were harvested three to seven (3-7) days after transfection. Supernatants were stored at reduced temperature (e.g. −80° C.).

General information regarding the recombinant expression of human immunoglobulins in e.g. HEK293 cells is given in: Meissner, P. et al., Biotechnol. Bioeng. 75 (2001) 197-203.

The protein concentration was determined by measuring the optical density (OD) at 280 nm, using the molar extinction coefficient calculated on the basis of the amino acid sequence. Purity was analyzed by SDS-PAGE in the presence and absence of a reducing agent (5 mM 1,4-dithiotreitol) and staining with Coomassie brilliant blue.

Example 3

Sortase Mediated Conjugation

A reaction mixture comprising 100 μM Fc-region fragment comprising a C-terminal LPETG Sortase motif (SEQ ID NO: 30), 100 μM Fc-region fragment containing an N-terminal triple-alanine motif (SEQ ID NO: 27) and 10 μM *Staphylococcus aureus* Sortase A in 50 mM Tris pH 7.5, 150 mM NaCl, 5 mM CaCl$_2$ was incubated at 37° C. for 40 hours.

In the samples taken after 16 hours and 40 hours the reaction was stopped by heating to 90° C.

The samples (32.5 μl) supplemented with 5 μl reducing agent (Novex) and 12.5 μl sample buffer (Novex) were incubated for 10 min. at 90° C. 20 μl of each preparation were loaded on a 4-12% Bis-Tris gradient gel (Novex). The gel electrophoresis was carried out in 1×MOPS buffer (Novex) at 200 V and 120 mA for 35 min.

Example 4

Sortase Activity Assay

With the method as outlined below the activity of a Sortase-mediated enzymatic conjugation/coupling reaction can be determined photometricly by fusing a glucose dehydrogenase as reporter enzyme to a sortase amino acid motif (LPETG or LPETA) and using this as first substrate. As second substrate biotinylated oligo-glycin or oligo-alanine is used (nucleophile). When the Sortase is added to a solution containing the first and the second substrate a conjugate is formed by sortase-mediated conjugation of the first and the second substrate which is a biotinylated reporter enzyme. The biotinylated reporter enzyme can be recovered using a streptavidin-coated magnetic beads. When a substrate for the reporter enzyme is added, the product can be detected by the change of optical density.

Purified Sortase was mixed with its substrates, i.e. a glucose dehydrogenase containing the LPETG or LPETA motif (20 μM) and a biotin derivative containing N-terminal glycines or alanines (330 μM) in 50 mM Tris buffer pH 7.5 containing 200 mM NaCl. The reaction mixture was incubated at 37° C. for two hours. The reaction was stopped by addition of a 10-to 20-fold excess of inhibition buffer (50 mM Tris, pH 7.5, 200 mM NaCl, 10 mM $CaCl_2$, 5 mM iodoacetamide). The stopped reaction mixture was centrifuged for 10 min. at 5000×g. The supernatant (50 μL) was added to 100 μL of 50 mM Tris buffer (pH 7.5) comprising 200 mM NaCl, 10 mM $CaCl_2$ and streptavidin coted magnetic beads were added and incubated for 30 min. at 30° C. at 200 rpm. Thereafter the magnetic beads were washed five times with 300 μL washing buffer each (50 mM Tris, pH 7.5, 200 mM NaCl, 10 mM $CaCl_2$, 5 mg/mL BSA, 0.1% Triton X-100) in V-bottom multi-well plates using a magnet and a vacuum pump. Afterwards the beads are resuspended in 100 μL citrate test buffer and 10-80 μL thereof were transferred to a new well. Thereto 150 μL test buffer (0.2 M sodium citrate, pH 5.8, 0.3 g/L 4-nitrosoanilin, 1 mM CaCl2, 30 mM glucose) was added.

The kinetic of the reporter enzyme is measured over a time period of 5 min. at 620 nm. The activity of the reporter enzyme is proportional to the amount of immobilized enzyme, which is proportional to the amount of biotinylated enzyme and this is proportional to the activity of the sortase.

Example 5

Analyzing Product Formation and Degradation by Sortase Activity Assay

Indicated concentrations of Sa-SrtA, a glucose dehydrogenase containing the LPKTG sortase motif and GGGG-biotin or AAAA-biotin where incubated for indicated time points. The reaction was stopped and analyzed following the procedure as outlined in Example 4 using magnetic beads. For the reaction with 10 μM biotin the reaction mixture was stopped with 20 fold excess of inhibition buffer, the one with 100 μM biotin was stopped with 100 fold excess of inhibition buffer. The measured activity (dE/min) is proportional to the yield of the sortase reaction. For each reaction condition the highest yield was set to 100%. The yields at other time points were normalized to the 100%.

Figure 3:
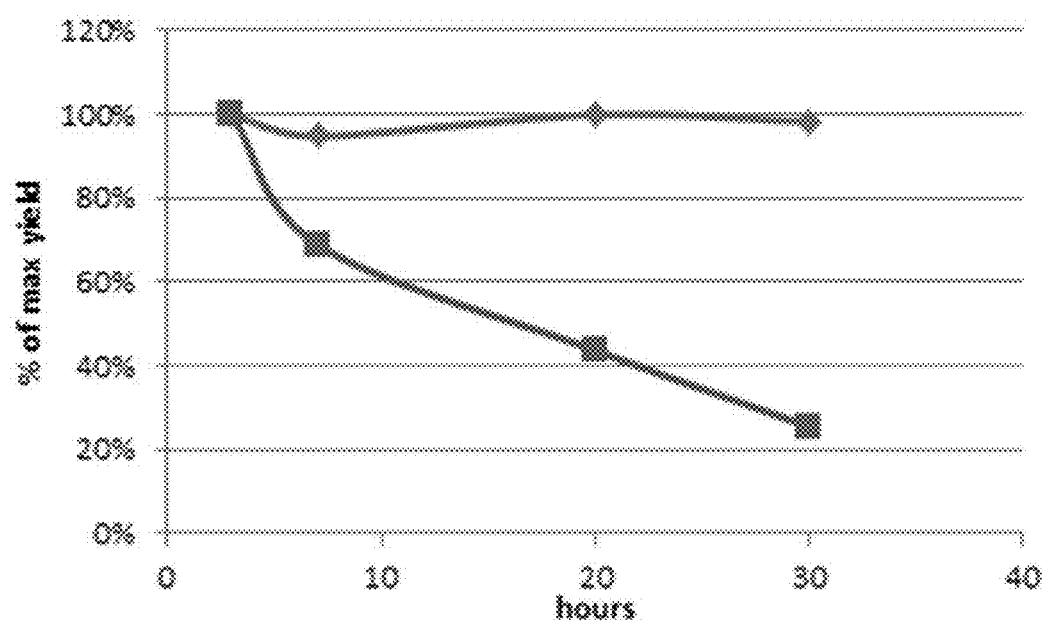
FIG. 3 Time course of maximum yield depending on the used substrates; square: LPKTG+G, diamond: LPKTG+A.

Experiment 1 (FIG. 3)

Starting materials were 120 μM LPKTG containing protein, 500 μM *staphylococcus aureus* Sortase A, 10 μM GGGG-biotin/AAAA-biotin.

| time [h]  | 3    | 7   | 20   | 30  |
|-----------|------|-----|------|-----|
| LPKTG + A | 100% | 95% | 100% | 98% |
| LPKTG + G | 100% | 69% | 44%  | 25% |

Figure 4:
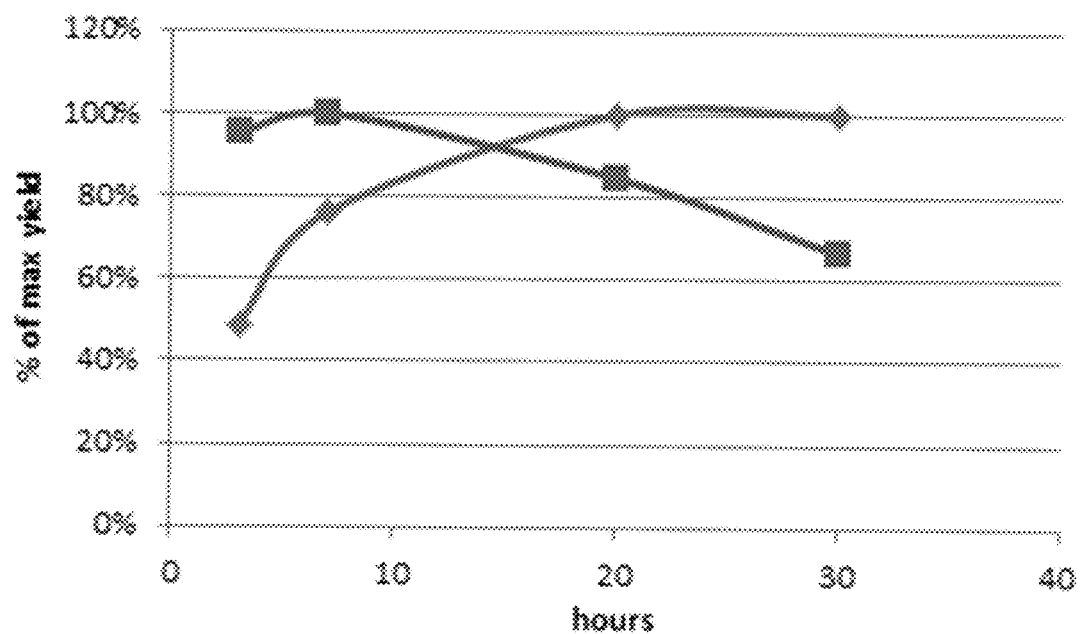
FIG. 4 Time course of maximum yield depending on the used substrates; square: LPKTG+G, diamond: LPKTG+A.

Experiment 2 (FIG. 4)

Starting materials were 20 μM LPKTG containing protein, 125 μM *staphylococcus aureus* Sortase A, 100 μM GGG/AAA.

|           | 3    | 7    | 20   | 30   |
|-----------|------|------|------|------|
| LPKTG + A | 49%  | 76%  | 100% | 100% |
| LPKTG + G | 95%  | 100% | 85%  | 67%  |

The invention claimed is:

1. A method for producing an enzymatic conjugation product of two polypeptides comprising the following steps
   incubating
   i) a first polypeptide comprising the amino acid sequence LPXTG (SEQ ID NO: 20, wherein X can be any amino acid residue),
   ii) a second polypeptide that comprises i) an alaninyl compound at its N-terminus, or ii) an oligo-alanine $A_m$ (m =2 (SEQ ID NO: 26), or 3 (SEQ ID NO: 27), or 4 (SEQ ID NO: 28), or 5 (SEQ ID NO: 29)), or iii) a cysteine amino acid residue followed by one to three alanine amino acid residues at its N-terminus,
   iii) a third polypeptide with sortase activity which is derived from *Staphylococcus aureus* Sortase A, and recovering the conjugate from the reaction mixture and thereby producing the enzymatic conjugation product of two polypeptides.

2. The method according to claim 1, wherein the first polypeptide comprises at its C-terminus the amino acid sequence LPXTG (SEQ ID NO: 20, wherein X can be any amino acid residue).

3. The method according to claim 2, wherein the first polypeptide comprises at its C-terminus the amino acid sequence LPETG (SEQ ID NO: 30).

4. The method according to claim 3, wherein the second polypeptide has an oligo-alanine of SEQ ID NO: 26 or SEQ ID NO: 27 at its N-terminus.

5. The method according to claim 3, wherein the first polypeptide and the second polypeptide are independently of each other selected from an antibody variable domain, an antibody heavy chain Fab-fragment, an antibody Fc-region, a tag, and a peptide comprising the amino acid sequence LPXTG (SEQ ID NO: 20, wherein X can be any amino acid residue), a linker and a non-Sortase motif moiety.

6. The method according to claim 3, wherein the third polypeptide has the amino acid sequence of SEQ ID NO: 21.

7. The method according to claim 2, wherein the second polypeptide has an oligo-alanine of SEQ ID NO: 26 or SEQ ID NO: 27 at its N-terminus.

8. The method according to claim 2, wherein the first polypeptide and the second polypeptide are independently of each other selected from an antibody variable domain, an antibody heavy chain Fab-fragment, an antibody Fc-region, a tag, and a peptide comprising the amino acid sequence LPXTG (SEQ ID NO: 20, wherein X can be any amino acid residue), a linker and a non-Sortase motif moiety.

9. The method according to claim 2, wherein the third polypeptide has the amino acid sequence of SEQ ID NO: 21.

10. The method according to claim 1, wherein the second polypeptide has an oligo-alanine of SEQ ID NO: 26 or SEQ ID NO: 27 at its N-terminus.

11. The method according to claim 10, wherein the first polypeptide and the second polypeptide are independently of each other selected from an antibody variable domain, an antibody heavy chain Fab-fragment, an antibody Fc-region, a tag, and a peptide comprising the amino acid sequence LPXTG (SEQ ID NO: 20, wherein X can be any amino acid residue), a linker and a non-Sortase motif moiety.

12. The method according to claim 10, wherein the third polypeptide has the amino acid sequence of SEQ ID NO: 21.

13. The method according to claim 1, wherein the first polypeptide and the second polypeptide are independently of each other selected from an antibody variable domain, an antibody heavy chain Fab-fragment, an antibody Fc-region, a tag, and a peptide comprising the amino acid sequence LPXTG (SEQ ID NO: 20, wherein X can be any amino acid residue), a linker and a non-Sortase motif moiety.

14. The method according to claim 13, wherein the third polypeptide has the amino acid sequence of SEQ ID NO: 21.

15. The method according to claim 1, wherein the third polypeptide has the amino acid sequence of SEQ ID NO: 21.

* * * * *

SEQUENCE LISTING

```
<160> NUMBER OF SEQ ID NOS: 31

<210> SEQ ID NO 1
<211> LENGTH: 5
<212> TYPE: PRT
<213> ORGANISM: Artificial Sequence
<220> FEATURE:
<223> OTHER INFORMATION: Arg-tag

<400> SEQUENCE: 1

Arg Arg Arg Arg Arg
1               5

<210> SEQ ID NO 2
<211> LENGTH: 6
<212> TYPE: PRT
<213> ORGANISM: Artificial Sequence
<220> FEATURE:
<223> OTHER INFORMATION: Arg-tag 2

<400> SEQUENCE: 2

Arg Arg Arg Arg Arg Arg
1               5

<210> SEQ ID NO 3
```

```
<211> LENGTH: 6
<212> TYPE: PRT
<213> ORGANISM: Artificial Sequence
<220> FEATURE:
<223> OTHER INFORMATION: His-tag

<400> SEQUENCE: 3

His His His His His His
1               5

<210> SEQ ID NO 4
<211> LENGTH: 19
<212> TYPE: PRT
<213> ORGANISM: Artificial Sequence
<220> FEATURE:
<223> OTHER INFORMATION: amino acid tag

<400> SEQUENCE: 4

Lys Asp His Leu Ile His Asn Val His Lys Glu Phe His Ala His Ala
1               5                   10                  15

His Asn Lys

<210> SEQ ID NO 5
<211> LENGTH: 8
<212> TYPE: PRT
<213> ORGANISM: Artificial Sequence
<220> FEATURE:
<223> OTHER INFORMATION: amino acid tag

<400> SEQUENCE: 5

Asp Tyr Lys Asp Asp Asp Asp Lys
1               5

<210> SEQ ID NO 6
<211> LENGTH: 22
<212> TYPE: PRT
<213> ORGANISM: Artificial Sequence
<220> FEATURE:
<223> OTHER INFORMATION: amino acid tag

<400> SEQUENCE: 6

Asp Tyr Lys Asp His Asp Gly Asp Tyr Lys Asp His Asp Ile Asp Tyr
1               5                   10                  15

Lys Asp Asp Asp Asp Lys
            20

<210> SEQ ID NO 7
<211> LENGTH: 9
<212> TYPE: PRT
<213> ORGANISM: Artificial Sequence
<220> FEATURE:
<223> OTHER INFORMATION: amino acid tag#

<400> SEQUENCE: 7

Ala Trp Arg His Pro Gln Phe Gly Gly
1               5

<210> SEQ ID NO 8
<211> LENGTH: 8
<212> TYPE: PRT
<213> ORGANISM: Artificial Sequence
<220> FEATURE:
<223> OTHER INFORMATION: amino acid tag

<400> SEQUENCE: 8

Trp Ser His Pro Gln Phe Glu Lys
```

```
1               5

<210> SEQ ID NO 9
<211> LENGTH: 10
<212> TYPE: PRT
<213> ORGANISM: Artificial Sequence
<220> FEATURE:
<223> OTHER INFORMATION: amino acid tag

<400> SEQUENCE: 9

Met Asp Val Glu Ala Trp Leu Gly Ala Arg
1               5                   10

<210> SEQ ID NO 10
<211> LENGTH: 16
<212> TYPE: PRT
<213> ORGANISM: Artificial Sequence
<220> FEATURE:
<223> OTHER INFORMATION: amino acid tag

<400> SEQUENCE: 10

Met Asp Val Glu Ala Trp Leu Gly Ala Arg Val Pro Leu Val Glu Thr
1               5                   10                  15

<210> SEQ ID NO 11
<211> LENGTH: 38
<212> TYPE: PRT
<213> ORGANISM: Artificial Sequence
<220> FEATURE:
<223> OTHER INFORMATION: amino acid tag

<400> SEQUENCE: 11

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 12
<211> LENGTH: 10
<212> TYPE: PRT
<213> ORGANISM: Artificial Sequence
<220> FEATURE:
<223> OTHER INFORMATION: amino acid tag

<400> SEQUENCE: 12

Glu Gln Lys Leu Ile Ser Glu Glu Asp Leu
1               5                   10

<210> SEQ ID NO 13
<211> LENGTH: 15
<212> TYPE: PRT
<213> ORGANISM: Artificial Sequence
<220> FEATURE:
<223> OTHER INFORMATION: amino acid tag

<400> SEQUENCE: 13

Lys Glu Thr Ala Ala Ala Lys Phe Glu Arg Gln His Met Asp Ser
1               5                   10                  15

<210> SEQ ID NO 14
<211> LENGTH: 26
<212> TYPE: PRT
<213> ORGANISM: Artificial Sequence
<220> FEATURE:
```

<223> OTHER INFORMATION: amino acid tag

<400> SEQUENCE: 14

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 15
<211> LENGTH: 47
<212> TYPE: PRT
<213> ORGANISM: Artificial Sequence
<220> FEATURE:
<223> OTHER INFORMATION: amino acid tag

<400> SEQUENCE: 15

Pro Ala Thr Thr Thr Gly Ser Ser Pro Gly Pro Thr Gln Ser His Tyr
1               5                   10                  15

Gly Gln Cys Gly Gly Ile Gly Tyr Ser Gly Pro Thr Val Cys Ala Ser
            20                  25                  30

Gly Thr Thr Cys Gln Val Leu Asn Pro Tyr Tyr Ser Gln Cys Leu
        35                  40                  45

<210> SEQ ID NO 16
<211> LENGTH: 32
<212> TYPE: PRT
<213> ORGANISM: Butyrivibrio fibrisolvens

<400> SEQUENCE: 16

Met Asp Trp Asn Ala Asn Ile Ala Pro Gly Asn Ser Val Glu Phe Gly
1               5                   10                  15

Ile Gln Gly Ala Gly Ser Val Gly Asn Val Ile Asp Ile Thr Val Glu
            20                  25                  30

<210> SEQ ID NO 17
<211> LENGTH: 51
<212> TYPE: PRT
<213> ORGANISM: Artificial Sequence
<220> FEATURE:
<223> OTHER INFORMATION: chitin-binding-domain

<400> SEQUENCE: 17

Thr Asn Pro Gly Val Ser Ala Trp Gln Val Asn Thr Ala Tyr Thr Ala
1               5                   10                  15

Gly Gln Leu Val Thr Tyr Asn Gly Lys Thr Tyr Lys Cys Leu Gln Pro
            20                  25                  30

His Thr Ser Leu Ala Gly Trp Glu Pro Ser Asn Val Pro Ala Leu Trp
        35                  40                  45

Gln Leu Gln
    50

<210> SEQ ID NO 18
<211> LENGTH: 209
<212> TYPE: PRT
<213> ORGANISM: Chondrus crispus

<400> SEQUENCE: 18

Met Pro Glu Ile Lys Leu Thr Tyr Phe Asp Met Arg Gly Arg Ala Glu
1               5                   10                  15

Ala Ser Arg Leu Ala Leu Val Val Gly Glu Ile Pro Phe Glu Asp Glu
            20                  25                  30

```
Arg Val Val Phe Asp His Trp Lys Glu Ala Lys Pro Lys Thr Pro Tyr
            35                  40                  45

Ala Ala Leu Pro Met Leu Thr Val Asp Gly Met Gln Val Ala Gln Ser
 50                  55                  60

Asp Ala Ile Leu Arg Tyr Cys Gly Lys Leu Ala Gly Leu Tyr Pro Ser
 65                  70                  75                  80

Asp Pro Leu Glu Ala Ala Lys Val Asp Glu Val Gly Val Ile Asp
                 85                  90                  95

Asp Val Thr His Ala Met Tyr Arg Tyr Arg Gly Asp Asp Lys Asp Lys
                100                 105                 110

Leu Arg Glu Glu Arg Asp Lys Phe Ser Lys Val Asp Val Pro Arg Tyr
        115                 120                 125

Val Gly Ala Leu Glu Lys Arg Leu Glu Ala Phe Gly Asp Gly Pro Trp
    130                 135                 140

Ala Val Gly Gly Asn Met Thr Ile Ala Asp Leu His Ile Cys His Leu
145                 150                 155                 160

Val Thr Asn Ile Arg Cys Gly Met Leu Asp Phe Val Lys Asp Leu
                165                 170                 175

Leu Glu Gly Tyr Val Arg Ile Val Lys Ser Tyr Ser Ala Val Met Glu
            180                 185                 190

His Pro Lys Val Thr Glu Trp Tyr Glu Lys Lys Pro Val Lys Met Phe
        195                 200                 205

Ser

<210> SEQ ID NO 19
<211> LENGTH: 396
<212> TYPE: PRT
<213> ORGANISM: Escherichia coli

<400> SEQUENCE: 19

Met Lys Ile Lys Thr Gly Ala Arg Ile Leu Ala Leu Ser Ala Leu Thr
  1               5                  10                  15

Thr Met Met Phe Ser Ala Ser Ala Leu Ala Lys Ile Glu Glu Gly Lys
                 20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
 50                  55                  60

His Pro Asp Lys Leu Glu Glu Lys Phe Pro Gln Val Ala Ala Thr Gly
 65                  70                  75                  80

Asp Gly Pro Asp Ile Ile Phe Trp Ala His Asp Arg Phe Gly Gly Tyr
                 85                  90                  95

Ala Gln Ser Gly Leu Leu Ala Glu Ile Thr Pro Asp Lys Ala Phe Gln
                100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190
```

```
Tyr Ala Phe Lys Tyr Glu Asn Gly Lys Tyr Asp Ile Lys Asp Val Gly
            195                 200                 205

Val Asp Asn Ala Gly Ala Lys Ala Gly Leu Thr Phe Leu Val Asp Leu
        210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
                260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Ile Ala Ala Thr Met Glu Asn Ala Gln Lys
                340                 345                 350

Gly Glu Ile Met Pro Asn Ile Pro Gln Met Ser Ala Phe Trp Tyr Ala
                355                 360                 365

Val Arg Thr Ala Val Ile Asn Ala Ala Ser Gly Arg Gln Thr Val Asp
                370                 375                 380

Glu Ala Leu Lys Asp Ala Gln Thr Arg Ile Thr Lys
385                 390                 395

<210> SEQ ID NO 20
<211> LENGTH: 5
<212> TYPE: PRT
<213> ORGANISM: Artificial Sequence
<220> FEATURE:
<223> OTHER INFORMATION: Sortase motif amino acid sequence
<220> FEATURE:
<221> NAME/KEY: MISC_FEATURE
<222> LOCATION: (3)..(3)
<223> OTHER INFORMATION: Xaa = can be any of the 20 proteinogenic amino
      acids

<400> SEQUENCE: 20

Leu Pro Xaa Thr Gly
1               5

<210> SEQ ID NO 21
<211> LENGTH: 147
<212> TYPE: PRT
<213> ORGANISM: Artificial Sequence
<220> FEATURE:
<223> OTHER INFORMATION: mature soluble sortase

<400> SEQUENCE: 21

Gln Ala Lys Pro Gln Ile Pro Lys Asp Lys Ser Lys Val Ala Gly Tyr
1               5                   10                  15

Ile Glu Ile Pro Asp Ala Asp Ile Lys Glu Pro Val Tyr Pro Gly Pro
            20                  25                  30

Ala Thr Pro Glu Gln Leu Asn Arg Gly Val Ser Phe Ala Glu Glu Asn
        35                  40                  45

Glu Ser Leu Asp Asp Gln Asn Ile Ser Ile Ala Gly His Thr Phe Ile
    50                  55                  60
```

Asp Arg Pro Asn Tyr Gln Phe Thr Asn Leu Lys Ala Ala Lys Lys Gly
 65                  70                  75                  80

Ser Met Val Tyr Phe Lys Val Gly Asn Glu Thr Arg Lys Tyr Lys Met
                 85                  90                  95

Thr Ser Ile Arg Asp Val Lys Pro Thr Asp Val Gly Val Leu Asp Glu
            100                 105                 110

Gln Lys Gly Lys Asp Lys Gln Leu Thr Leu Ile Thr Cys Asp Asp Tyr
        115                 120                 125

Asn Glu Lys Thr Gly Val Trp Glu Lys Arg Lys Ile Phe Val Ala Thr
    130                 135                 140

Glu Val Lys
145

<210> SEQ ID NO 22
<211> LENGTH: 2
<212> TYPE: PRT
<213> ORGANISM: Artificial Sequence
<220> FEATURE:
<223> OTHER INFORMATION: oligoglycine motif

<400> SEQUENCE: 22

Gly Gly
1

<210> SEQ ID NO 23
<211> LENGTH: 3
<212> TYPE: PRT
<213> ORGANISM: Artificial Sequence
<220> FEATURE:
<223> OTHER INFORMATION: oligoglycine motif

<400> SEQUENCE: 23

Gly Gly Gly
1

<210> SEQ ID NO 24
<211> LENGTH: 4
<212> TYPE: PRT
<213> ORGANISM: Artificial Sequence
<220> FEATURE:
<223> OTHER INFORMATION: oligoglycine motif

<400> SEQUENCE: 24

Gly Gly Gly Gly
1

<210> SEQ ID NO 25
<211> LENGTH: 5
<212> TYPE: PRT
<213> ORGANISM: Artificial Sequence
<220> FEATURE:
<223> OTHER INFORMATION: oligoglycine motif

<400> SEQUENCE: 25

Gly Gly Gly Gly Gly
1               5

<210> SEQ ID NO 26
<211> LENGTH: 2
<212> TYPE: PRT
<213> ORGANISM: Artificial Sequence
<220> FEATURE:
<223> OTHER INFORMATION: oligoalanine motif

<400> SEQUENCE: 26

```
Ala Ala
1

<210> SEQ ID NO 27
<211> LENGTH: 3
<212> TYPE: PRT
<213> ORGANISM: Artificial Sequence
<220> FEATURE:
<223> OTHER INFORMATION: oligoalanine motif

<400> SEQUENCE: 27

Ala Ala Ala
1

<210> SEQ ID NO 28
<211> LENGTH: 4
<212> TYPE: PRT
<213> ORGANISM: Artificial Sequence
<220> FEATURE:
<223> OTHER INFORMATION: oligoalanine motif

<400> SEQUENCE: 28

Ala Ala Ala Ala
1

<210> SEQ ID NO 29
<211> LENGTH: 5
<212> TYPE: PRT
<213> ORGANISM: Artificial Sequence
<220> FEATURE:
<223> OTHER INFORMATION: oligoalanine motif

<400> SEQUENCE: 29

Ala Ala Ala Ala Ala
1               5

<210> SEQ ID NO 30
<211> LENGTH: 5
<212> TYPE: PRT
<213> ORGANISM: Artificial Sequence
<220> FEATURE:
<223> OTHER INFORMATION: sortase motif

<400> SEQUENCE: 30

Leu Pro Glu Thr Gly
1               5

<210> SEQ ID NO 31
<211> LENGTH: 12
<212> TYPE: PRT
<213> ORGANISM: Artificial Sequence
<220> FEATURE:
<223> OTHER INFORMATION: purification tag

<400> SEQUENCE: 31

Met Arg Gly Ser His His His His His His Gly Ser
1               5                   10
```